United States Patent [19]
Detsch et al.

[11] Patent Number: 6,019,117
[45] Date of Patent: *Feb. 1, 2000

[54] WATER LINE DECONTAMINATION SYSTEM

[76] Inventors: Steven G. Detsch, 4115 The Hill Rd., Bonita, Calif. 91902; Scott L. Preston, 1127 Fair Oaks, Arroyo Grande, Calif. 93420

[ * ] Notice: This patent is subject to a terminal disclaimer.

[21] Appl. No.: 08/633,245

[22] Filed: Apr. 16, 1996

Related U.S. Application Data

[63] Continuation of application No. 08/109,622, Aug. 20, 1993, Pat. No. 5,526,841.

[51] Int. Cl.[7] ............................. B08B 3/04; B08B 5/00; B08B 9/02
[52] U.S. Cl. ..................... 137/15; 134/30; 134/95.1; 134/95.2; 134/102.2; 134/102.3; 134/169 C; 134/171; 137/240; 222/148
[58] Field of Search ................ 134/26, 30, 94.1, 134/95.1, 95.2, 99.1, 100.1, 102.1, 102.2, 102.3, 167 C, 169 C, 169 R, 171; 137/240, 241; 222/148

[56] References Cited

U.S. PATENT DOCUMENTS

| | | | |
|---|---|---|---|
| 3,625,231 | 12/1971 | Littrell | 134/102 |
| 3,650,678 | 3/1972 | Hansen | 21/91 |
| 3,811,408 | 5/1974 | Thompson | 118/73 |
| 4,193,818 | 3/1980 | Young et al. | 134/1 |
| 4,502,614 | 3/1985 | Weller et al. | 222/148 |
| 4,572,230 | 2/1986 | Mirabile | 137/240 |
| 4,582,226 | 4/1986 | Doak | 137/240 |
| 4,892,112 | 1/1990 | Knetsch | 134/102 |
| 4,941,593 | 7/1990 | Hicks et al. | 137/240 |
| 4,979,527 | 12/1990 | Mueller et al. | 137/240 |
| 5,090,440 | 2/1992 | Ladouceur et al. | 137/240 |

*Primary Examiner*—George L. Walton
*Attorney, Agent, or Firm*—Lyon & Lyon LLP

[57] ABSTRACT

A water line decontamination unit has inlets for connection to a supply of irrigant liquid, a supply of disinfectant, and a pressurized gas supply, and an outlet for connection to a water line inlet. A valve assembly in the unit controls the supply of irrigant liquid, disinfectant and gas to the water line so that only one of the fluids is supplied to the water line at any one time. A manual selector allows an operator to select a run condition in which irrigant liquid is supplied to the water line, a flush condition in which disinfectant is supplied to the water line, and a purge condition in which gas is supplied to purge liquid from the water line.

28 Claims, 3 Drawing Sheets

WATER LINE DECONTAMINATION SYSTEM

RELATED APPLICATION

This application is a continuation of U.S. Ser. No. 08/109,622 filed Aug. 20, 1993, now U.S. Pat. No. 5,526,841, the disclosure of which is specifically incorporated herein by reference.

BACKGROUND OF THE INVENTION

The present invention relates generally to a water supply decontamination system, and is particularly concerned with a decontamination system for water lines used in dental offices and other medical facilities.

Water supplies in all health care facilities have the potential for contamination by disease causing bacteria and viruses. The municipal water supply is known to carry certain bacteria, but the bacteria are usually present in such low numbers that they present no hazard. However, when such water is supplied to a dental water line, and stands in the line for extended periods, a bacterial biofilm forms on the plastic tubing due to the very high surface area to volume ratio of the tubing. The biofilm acts as a breeding ground for such disease producing bacteria as Pseudonomas, Klebsiella and Legionella. In addition, contamination also occurs from "suck-back" of fluids from the patient's mouth into the dental handpiece. As a result, water supplied from a dental water line to rinse a patient's mouth is often grossly contaminated and would not meet the standards required for municipal drinking water.

A fine aerosol mist is created by dental handpieces and the like, so that bacteria present in the water line are dispersed into the air and will be inhaled by both patient and dental personnel. This allows bacteria to enter the respiratory tract and has been shown to lead to infection or disease in some cases.

Another problem arising from the build-up of a biofilm in dental or other medically used water lines is that the biofilm is liable to spread back from the contaminated water line and into the building water supply lines. This has been shown to have occurred in some buildings, and such contamination is extremely difficult to eliminate.

The American Dental Association recommends flushing dental water lines for two minutes or more at the start of each day and before each patient. However, this has not proved to be sufficient to remove the source of contamination, which is the biofilm formed as a coating on the water line. Thus, after flushing, testing has shown that the dental unit water line water still regularly fails to meet the U.S. public health requirements for potable water (i.e. 500 C.F.R. s/ml).

Another solution which has been tried is to supply water to the lines from a sterile source, rather than using the municipal water supply. However, contamination of the line and water reservoir can still occur as a result of suck-back or retraction of fluids from the patient's mouth. Bacterial growth will be amplified as a result of the water standing in the line, and growth of a biofilm will eventually occur.

Another method which has been proposed to deal with this problem is to provide a bacterial filter on the delivery side of the water supply line. Again, this does not deal with the problem of the biofilm formed on the water supply line, and will itself become a source of patient cross-contamination if not changed frequently, due to bacterial growth directly on the filter. Additionally, although it serves as a barrier to suck-back contamination, bacteria caught on the filter from a patient's mouth may be flushed into the next patient's mouth. This is no different than if it merely flowed into the water lines.

Another approach is to disinfect the dental water line using sterilizing agents. However, this does not always eliminate the biofilm, from which bacteria break off and provide a source of contamination to water subsequently flowing through the line, and is inconvenient and time consuming with existing systems. Also, cross-contamination between patients is still possible.

Up to now, no effective and convenient method or system for effectively decontaminating dental and other water lines has been proposed. However, such a system is clearly needed in view of the potential for both patients and medical personnel to contract diseases as a result of contamination of such water lines.

SUMMARY OF THE INVENTION

It is an object of the present invention to provide new and improved method and system for decontaminating after lines.

According to one aspect of the present invention, a after line decontamination system is provided, which comprises a water supply, a disinfectant supply, a source of pressurized gas such as air, and a selector valve assembly having a first inlet connected to the water supply, a second inlet connected to these disinfectant supply, a third inlet connected to the pressurized gas source, and an outlet for connection to -he inlet of a water line. The selector valve assembly includes valves for selectively controlling the connection of the water supply, the disinfectant supply and the pressurized gas source to the outlet. In a preferred embodiment of the invention, the water supply and disinfectant supply each comprise a container or bottle for containing water and a suitable disinfectant liquid, respectively, and a selector valve is provided in the valve assembly for controlling the connection of the pressurized gas source to the two containers so as to selectively supply water or disinfectant under pressure to the outlet in run and flush conditions, respectively, of the system. The selector valve also controls the connection of the pressurized gas inlet directly to the outlet in a purge condition of the system.

With the selector valve in the "run" position, water is supplied to the water line on activation of a high speed drill, dental syringe, or other tool connected to the water line. Following a dental procedure, the selector valve member is moved to the "purge" position, in which pressurized air clears both unit water and patient source contaminated fluids from the dental line. The selector valve member is then moved to the "flush" position in which disinfectant flows into the dental line when the dental drill or syringe is activated. When disinfectant flows out of the dental tools the user knows that the water lines are full. The disinfectant is then allowed to stand in the line for a recommended sterilization time. The disinfectant may stand in the lines until the unit is used on the next patient or overnight. The selector valve is preferably biassed from the flush position back to the purge position, so that after each flush cycle the selector valve member is moved back to the purge position so that pressurized air flushes all disinfectant from the line. This ensures that an operator does not accidentally supply an unrestricted amount of disinfectant to the patient's mouth. After the line is purged, the valve member is moved to the run position to flush water through the line.

In the preferred embodiment, the water supply is a container of sterile water, however, the standard water supply may be used in conjunction with a sterile bacteria filter. A similar container of disinfectant is provided for the disinfectant supply, with each container selectively connected to the pressurized air source in order to supply water or disinfectant to the water line. The disinfectant is preferably colored so that the user can easily determine when the water lines are full of disinfectant. A bacterial filter acting as a biologic check valve may be located at the outlet of the selector valve assembly as a means of isolating the system from contamination within the water lines or from patients.

Any liquid sterilant may be used, such as chlorine, chlorox, chlorhexidine gluconate (Peridex), chlorine dioxide, ethanol, quaternary ammonium compounds, and the like. The sterilant may be of the type usable as a mouthwash, and may also be supplied to the patient's mouth to disinfect the oral cavity prior to or during a dental procedure. The CDC has recommended that anti-microbial pre-rinses will reduce the risk to staff of bacterial infection from patients during dental procedures.

According to another aspect of the present invention, a method of decontaminating water lines for connection to surgical or dental instruments is provided, which comprises the steps of connecting the water line to a supply of sterile water in a run operation during a medical or dental procedure, connecting the water line to a source of pressurized gas on completion of the procedure to purge water and contaminants from the water line in a purge operation, connecting the water line to a disinfectant supply after water has been purged from the line to flush disinfectant through the line in a flush operation, and allowing disinfectant to stand in the line for a predetermined time period.

After the predetermined time period, the line may be purged with pressurized gas or air for a sufficient time period to completely dry the line. It is then ready for re-filling with water. Alternatively, disinfectant may be run through the line again and even supplied to the patient's mouth where it is of the type suitable for use as a disinfecting mouthwash. A means of isolation of the system from water line contamination is also incorporated.

A second alternative method is to purge the line with pressurized gas or air and thoroughly dry the lines for storage overnight. This dry environment eliminates the water stagnation which fosters biofilm growth. Desiccation may be as effective as chemical control to stop biofilm growth.

This decontamination system is easy and convenient to install on existing dental units using standard dental air lines and water lines. It provides an effective way for substantially reducing dental water line contamination. This will considerably reduce the risk of bacterial infection and transmission of other disease causing agents to both patients and dental or medical personnel.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENT

Figure 1:
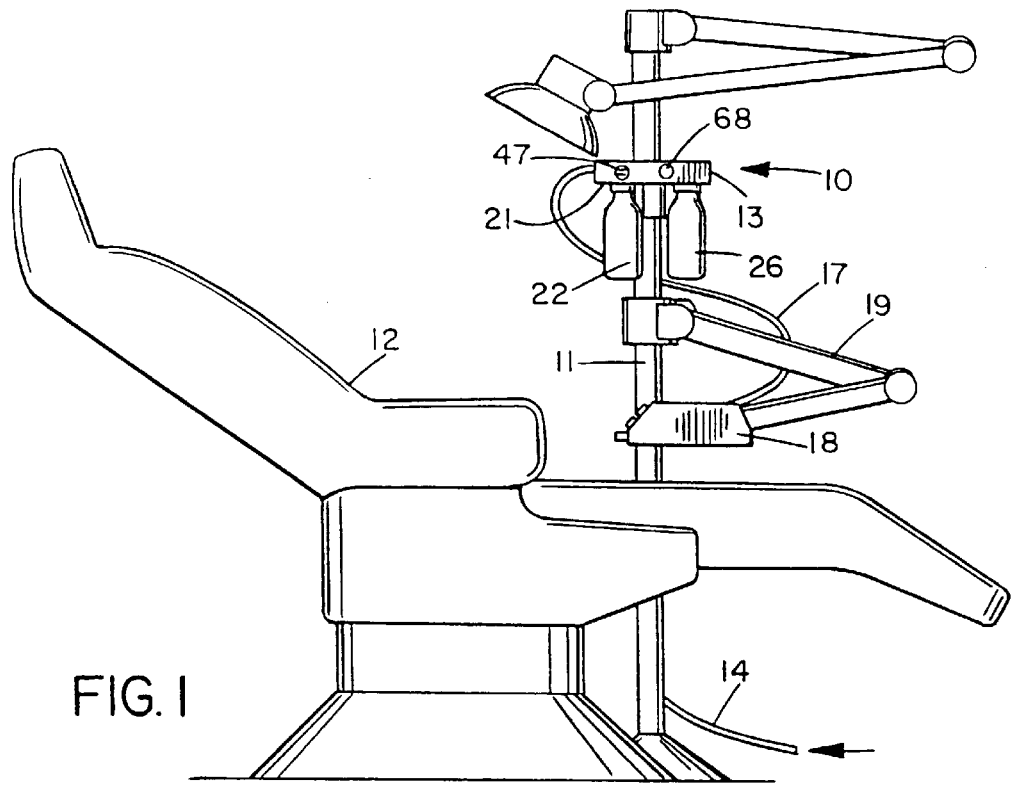
FIG. 1 is a side elevational view illustrating one possible installation of a decontamination unit according to a preferred embodiment of the invention on a dental chair unit.
Figure 2:
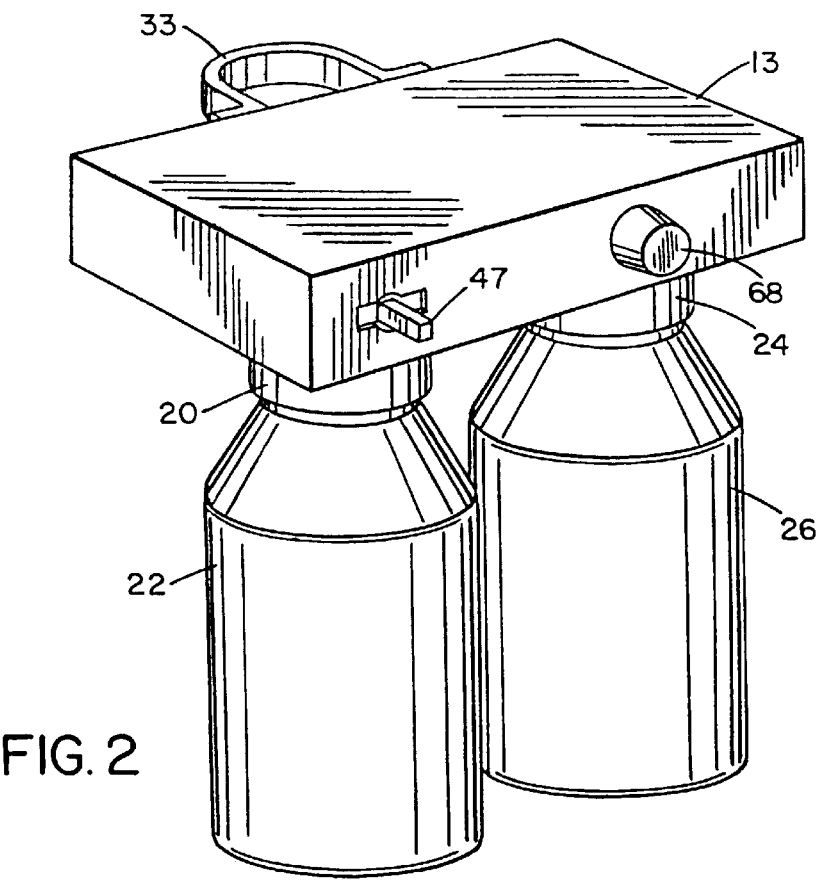
FIG. 2 is a perspective view of the decontamination unit.

FIG. 1 illustrates the water line decontamination unit 10 installed on a dental light supporting pole 11 of a dental chair unit 12. The unit 10 is designed for pole mounting or may alternatively be bolted to the undersurface of a dental cart unit carrying various dental tools, and plumbed into the existing water and air lines of the unit.

The unit 10 basically comprises an outer housing 13 designed for pole mounting or mounting on a dental cart unit, and having an air or gas inlet 14 for connection to a pressurized air supply, an air outlet; 15 and water outlet 16 for connection to a dental water line 17. As illustrated in FIG. 1, line 17 is connected and incorporated into a dental tool unit 18 on articulating arm 19.

The housing has a first adapter 20 in lower wall 21 for mounting a bottle 22 or other container for sterile water, and a second adapter 24 for mounting a bottle 26 or other container for a selected disinfectant. Each adapter has an inlet 28, 30, respectively, for pressurizing the container and an outlet 32, 34 for flow of liquid from the container under pressure. The adapters preferably have threaded bores for receiving the threaded necks of bottles 22, 26. A clamp ring 33 is provided for attaching the unit to a 211 round post, which is standard in the dental field. Screw holes (not illustrated may be drilled in the top of housing 13 So that it can be attached via screws to the undersurface of a dental cart unit.

Figure 3:
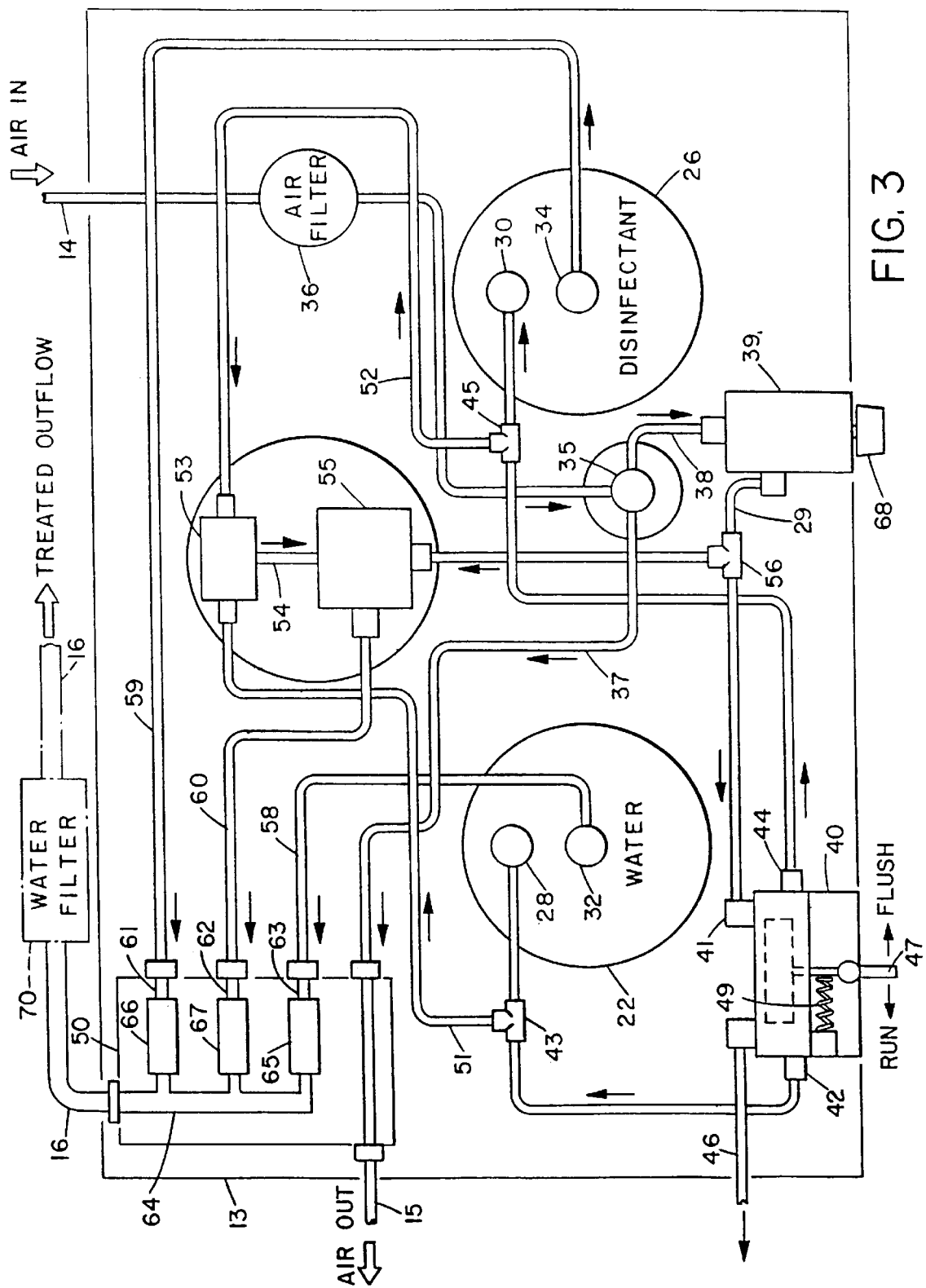
FIG. 3 is a block diagram illustrating the components of the decontamination unit and their interconnection.
Figure 4:
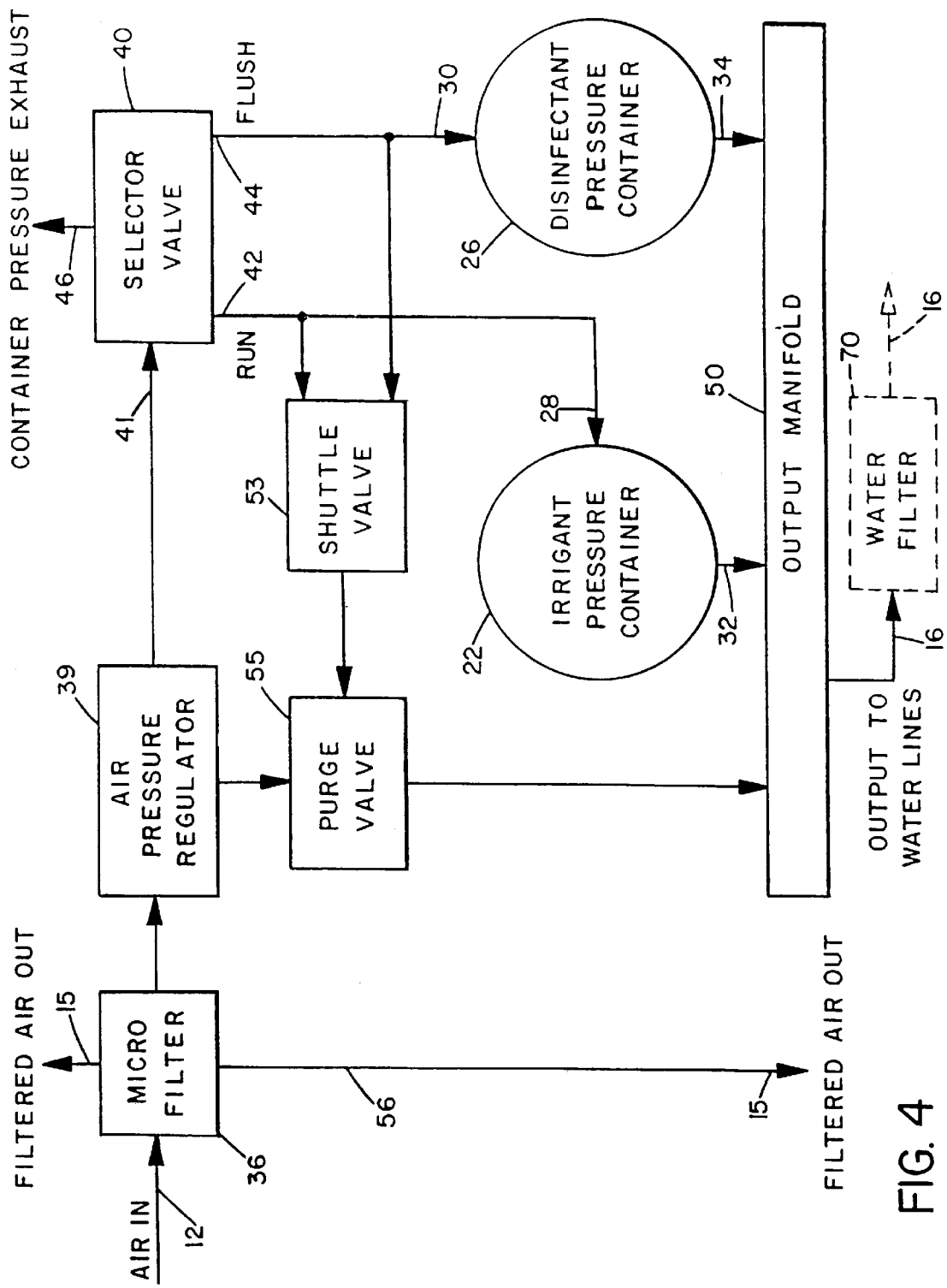
FIG. 4 is a schematic block diagram illustrating flow of gas and liquid through the unit.

As best illustrated in FIG. 3, the pressurized air inlet 14 is connected through a 0.01 micron air microfilter 36 to a T-junction 35 having outlet lines 37 and 38. One outlet line 37 is connected through an outlet manifold 50 to an air outlet 15 for connection to the dental unit air line or to a three-way syringe. The other outlet line 38 is connected through air pressure regulator 39 and line 29 to the inlet 41 of a three position, four-way selector valve 40 for selectively connecting the air inlet 12 to one of two outlets 42 and 44. Selector valve 40 is preferably a normally open, three position, fourway, center vented toggle valve having a run position in which the air inlet 12 is connected to outlet 42, a flush position in which the air inlet is connected to outlet 44, and a purge position in which the inlet 41 is cut off and air is exhausted from the containers via an exhaust outlet 46. A toggle 47 on the front of the housing controls the position of the valve. A biassing spring 49 biases the valve from the flush position to the purge position.

The outlets 42 and 44 are connected via T-junctions 43 and 45, respectively, to the pressurized air inlets 28 and 30, respectively, of the water and disinfectant pressure containers 22 and 26. The other outlets 51, 52 respectively, from each of the T-junctions 43, 45 are connected to opposite sides of a further shuttle valve 53. The outlet 54 of shuttle valve 53 is connected to an inlet of purge valve 55. Air line 29 also has a T-junction 56 connecting the line to purge valve 55. The shuttle valve 53 is an exhausting double check valve which is opened by pressure in either of the connecting lines from outlets 51 or 52, but which is closed when there is no pressure at either inlet.

Outlets 32 and 34 from the water and disinfectant containers 22,26 are each connected via lines 58, 59 to output selector manifold 50 and from the manifold 50 to the housing outlet 16 to the water line. Purge valve 55 also has an output line 60 connected through manifold 50 to outlet 16. Valve 55 is a normally open, three-way pilot valve which is closed under pressure from either of the run or flush air lines 51 or 52.

The output selector manifold 50 is illustrated in detail in FIG. 3. Manifold 50 has three inlet passage-ways 61, 62, 63 connected in parallel to a single outlet passageway 64 in communication with the housing outlet 16. The inlet passageways 63, 61, 62 are connected to water run outlet line 58, disinfectant or f lush outlet line 59, and purge valve or purge outlet line 60, respectively, and each passageway contains a check valve 65, 66, 67, respectively, which is normally closed.

Air from the dental unit supply enters the microfilter which preferably filters the air to 0.01 micron. Filtered air flow continues through the air pressure regulator, which reduces the pressure to 30 p.s.i. The regulator pressure may be varied via control knob 68. The air supply from the air pressure regulator is connected to the selector valve and to the purge valve via T-junction 56.

The toggle 47 can be moved by the operator into any one of three possible valve positions: PURGE, RUN or FLUSH, and is biassed from the FLUSH position into the PURGE position, via spring 49, as illustrated in FIG. 3.

When the selector valve is in the PURGE position, no air flows out through the run or flush outlets of the selector valve. The purge valve will therefore be open and air will flow through the purge valve via line 60 to the manifold 50, forcing check valve 67 open so that pressurized air is supplied to the dental water line.

If the selector valve is moved to the RUN position, air input via line 41 will f low out of the run outlet 42 of the selector valve to the inlet 28 of the water container 22, and also to the purge valve Via shuttle valve 53, closing the purge valve to cut off the air supply to the output manifold 50. The air will pressurize water container 22 to force water out via outlet 32, where it flows through line 58 and passageway 63 of the outlet manifold to the dental water line.

When the selector valve is moved to the FLUSH position, air will flow from inlet 41 through the selector valve to the flush outlet 44, supplying pressurized air to the inlet 30 of the disinfectant bottle 26 and simultaneously closing the purge valve 55. Disinfectant will flow out of the bottle 26 through outlet 34 and line 59 to the outlet manifold, opening check valve 66 and flowing through the manifold and via the outlet 16 to the dental water line. The toggle 47 must be held by the operator in the FLUSH position or it will be biassed back into the PURGE position automatically, cutting off the disinfectant supply. This is for safety reasons, and ensures that operators cannot accidentally leave the valve in the FLUSH position and supply unlimited disinfectant to the patient's mouth.

Thus, the system allows the operator to selectively run water or disinfectant through the water line 17, or to purge liquid from the line and replace it with pressurized air. This allows the water line to be disinfected and decontaminated at a precise disinfectant concentration quickly and easily between dental procedures, and provides a means for biofilm removal or control in the water line if properly used. In the preferred embodiment, a microfilter 70 is provided at outlet 16 for filtering-the water to 0.2 micron, isolating the valve housing from dental unit water line bacterial contamination by acting as a biologic check valve. Water may flow through but bacterial may not flow back through filter 70. The microfilter 70 may be any suitable bacterial filter, such as the SteriLine cartridge developed by SciTech Dental of Bellevue, Wash., which filters out particles as small as 0.2 microns. Since the line is purged of liquid and dried before supplying disinfectant, the disinfectant concentration can be precisely controlled at rated levels, ensuring effective killing of bacteria.

A preferred method of using the system will now be described. The system is connected to a dental unit air supply at air inlet 14 at a point where it can be shut off via the delivery system master switch. Thus, the system is activated by turning on the dental office air compressor. The existing syringe air and water lines of the dental unit are disconnected and rerouted to the decontamination unit air outlet 15 and water outlet 16. When not in use, the toggle switch is left in the PURGE position. To fill the water lines, the switch is moved to the RUN position, supplying water from container 22 to the water lines as described above. After completion of a dental procedure, the switch is moved to the PURGE position, causing pressurized air to purge water from the water lines. This has the advantages of preventing further water line contamination from patient fluid suck-back and cross-contamination between patients, in addition to allowing follow on precise disinfectant concentration to be added to the lines. Once air can be felt coming from the exit end of the water line, the system has been purged and the switch is moved to the FLUSH position and held manually in that position. This supplies disinfectant at precise concentration from bottle 26 to the water line. When disinfectant flows out of any dental tool connected to the water line, the lines are full of disinfectant. The disinfectant may be colored to allow visual observation of when the lines are full. The air compressor may then be turned off and the toggle switch released, leaving the disinfectant standing in the water line for a predetermined decontamination period. The decontamination period will depend on the disinfectant being used, and may typically be around 10 minutes between patients. More thorough decontamination or sterilization may be achieved by allowing disinfectant to stand in line overnight (in excess of 10 hours). Alternatively, the line may be purged and left dry and empty overnight. This results in desiccation of any biofilm and would restrict further biofilm growth.

At the end of the sterilization period, the disinfectant is purged from the lines by turning on the air compressor with the toggle switch in the FURGE position.

The system is now ready for use again. The amount of disinfectant used for each flush cycle will depend on the total volume of tubing in the system. For example, a three handpiece cart unit with one three-way syringe will have about 30 feet of 1/e-inch diameter tubing. This will use about 2.5 ounces of disinfectant per flush cycle. After sterilizing the water lines, additional sterilant may be supplied to the patient's mouth to sterilize the oral cavity.

The unit may be connected to the office water supply rather than an independent supply of sterile water. In this case, a sterilizing means such as an additional 0.2 micron filter, flash heating unit, or ultra-violet sterilizing unit may be placed upstream of the unit in line with the water inlet. However, the system preferably uses commercially available bottles of sterile water or saline which can be screwed into the adapter on the housing unit as described above.

The water and disinfectant bottles are preferably transparent or translucent and may be graduated so that the fluid levels can be read directly by observation. When empty, the bottles are unscrewed from the adapters and refilled or replaced. The 0.2 micron filter or filters, if used, should be replaced daily. The disinfectant bottle can be filled with acid, bases, detergents and bioenzymes to remove biofilms, calcifications and other contaminants from the water lines periodically by specific protocol for maintenance purposes. One possible protocol would be to fill the line with chlorine bleach or 10% muriatic acid once a week, and leave the unit overnight before purging the lines. The bottles are preferably plastic, screw-neck bottles which are rated to at least 100 p.s.i. The water bottle may optionally be filled with a medicating solution instead of sterile water or saline for in-situ continuous irrigation of medication into surgical sites or into gingival sulci during periodontal root planning and standard dental cleanings to reduce or eliminate bacterial infection. Suitable medicating solutions are tetracycline, chlorhexidine, chlorine dioxide, iodine solutions and the like.

The dental line decontamination unit of this invention provides a means of limiting cross-contamination due to residual water or patient fluids in the delivery system or dental unit water lines. This system provides relatively sterile water or other fluids to the oral cavity of a patient during dental procedures, and considerably reduces the risk of any transmission of bacterial or viral infection to patient or dental personnel as a result of water line contamination. It is compact, relatively inexpensive, and easy to install and use adjacent to any dental or medical unit.

Although a preferred embodiment of the invention has been described above by way of example only, it will be understood by those skilled in the field that, modifications may be made to the disclosed embodiment without departing from the scope of the invention, which is defined by the appended claims.

We claim:

1. A method of decontaminating a fluid line connected to a medical or dental device which dispenses water from a water supply through the fluid line, comprising the steps of:
   connecting the water supply to the fluid line through operation of a selective valve assembly;
   supplying the water to the fluid line through the selective valve assembly;
   disconnecting the water supply from the fluid line through operation of the selective valve assembly;
   connecting a second fluid supply to the fluid line through operation of the selective valve assembly; and
   supplying a second fluid to the fluid line through the selective valve assembly to break down biofilm in the fluid line.

2. A method of decontaminating a fluid line as recited in claim 1, wherein the second fluid is a disinfectant.

3. A method of decontaminating a fluid line as recited in claim 2, comprising the further step of allowing the disinfectant to stand in the fluid line for longer than a predetermined time period.

4. A method of decontaminating a fluid line as recited in claim 1, wherein the second fluid is a pressurized gas.

5. A method of decontaminating a fluid line as recited in claim 4, comprising the further steps of:
   using the pressurized gas to purge the water from the fluid line; and
   drying the fluid line for longer than a predetermined time period.

6. A decontamination system for a water line, comprising:
   a first inlet for connection to a water supply;
   a second inlet for connection to a second fluid supply;
   an outlet for connection to a fluid line inlet;
   a valve assembly for selectively connecting one of the first or the second inlets to the outlet while the other inlet is not connected to the outlet; and
   a controller for controlling the valve assembly so that water from the water supply is supplied to the outlet when the valve assembly is connected to the first inlet and a second fluid from the second fluid supply is supplied to the outlet when the valve assembly is connected to the second inlet;
   wherein biofilm in the water line is suppressed by supplying the second fluid to the outlet.

7. A decontamination system as recited in claim 6, wherein the second fluid is a disinfectant which flushes the water line to suppress biofilm development.

8. A decontamination system as recited in claim 6, wherein the second fluid is a pressurized gas which dries the water line to suppress biofilm development.

9. A fluid line decontamination system as recited in claim 6, wherein the valve assembly is comprised of two or more valves.

10. A decontamination system as recited in claim 6, wherein the water supply is comprised of sterile water.

11. A decontamination system as recited in claim 6, further comprising:
    a water supply line connected to the water supply; and
    sterilizing means placed upstream from the water supply in the water supply line.

12. A decontamination system for a water line, comprising:
    a first inlet for connection to a water supply;
    a second inlet for connection to a second fluid supply;
    a third inlet for connection to a third fluid supply;
    an outlet for connection to a fluid line inlet;
    a valve assembly for selectively connecting one of the first, second or third inlets to the outlet while the other two inlets are not connected to the outlet; and
    a controller;
    wherein the controller supplies water from the water supply to the outlet when the valve assembly is selectively connected to the first inlet, a second fluid from the second fluid supply to the outlet when the valve assembly is selectively connected to the second inlet and a third fluid from the third fluid supply to the outlet when the valve assembly is selectively connected to the third inlet;
    wherein biofilm development is suppressed by purging liquid from the water line when the valve assembly is connected to the third inlet.

13. A decontamination system as recited in claim 12, wherein liquid is purged from the water line by flushing the water line with a disinfectant fluid.

14. A fluid line decontamination system as recited in claim 13, wherein the disinfectant fluid is colored.

15. A decontamination system as recited in claim 12, wherein liquid is purged from the water line by a pressurized gas which dries the water line.

16. A decontamination system as recited in claim 12, wherein the water supply is comprised of sterile water.

17. A decontamination system as recited in claim 12, further comprising:
    a water supply line connected to the water supply; and
    sterilizing means placed upstream from the water supply in the water supply line.

18. A fluid line decontamination system as recited in claim 17, wherein the sterilizing means is comprised of a micro filter.

19. A decontamination system as recited in claim 12, further comprising a bacterial filter located at the outlet to isolate the system from the water line.

20. A decontamination system as recited in claim 12 wherein the water supply and the second fluid supply are disposable containers.

21. A decontamination system as recited in claim 12, wherein the valve assembly is comprised of two or more valves.

22. A decontamination system for a water line, comprising:
- a housing with a gas inlet for connection to a pressurized gas supply, a gas outlet and a housing outlet for connection to a fluid line inlet;
- a valve assembly with a first inlet for connection to a water supply, a second inlet for connection to a second fluid supply, a third inlet for connection to the pressurized gas supply through the gas inlet and a valve assembly outlet connected to the housing outlet; the valve assembly being capable of selectively connecting one of the first, second or third inlets to the housing outlet while the other two inlets are not connected to the housing outlet; and
- a controller that supplies a first fluid from the water supply to the housing outlet when the valve assembly is selectively connected to the first inlet, a second fluid from the second fluid supply to the housing outlet when the valve assembly is selectively connected to the second inlet and pressurized gas from the pressurized gas supply to the housing outlet when the valve assembly is selectively connected to the third inlet;
- wherein biofilm development is suppressed by purging liquid from the water line when the valve assembly is connected to the third inlet.

23. A fluid line decontamination system as recited in claim 22, further comprising a gas microfilter located at the gas inlet.

24. A fluid line decontamination system as recited in claim 23, further comprising:
- a pressurized line connecting the first and the second fluid supplies to the pressurized gas supply; and
- a pressure regulator located between the gas inlet and the first and the second fluid supplies to control the pressure of pressurized gas supplied to the first and second fluid supplies through the pressurized line.

25. A medical or dental apparatus, comprising:
- a dispensing device for dispensing a fluid;
- a fluid line connected at a first end to the dispensing device;
- a housing with a gas inlet for connection to a pressurized gas supply, a gas outlet and a housing outlet connected to a second end of the fluid line;
- a valve assembly with a first inlet for connection to a water supply, a second inlet for connection to a second fluid supply, and a valve assembly outlet connected to the housing outlet, the valve assembly being capable of selectively connecting either the first or the second inlet to the housing outlet while the other inlet is not connected to the housing outlet; and
- a controller that supplies a first fluid from the first fluid supply to the housing outlet when the valve assembly is selectively connected to the first inlet and a second fluid from the second fluid supply to the housing outlet when the valve assembly is selectively connected to the second inlet;
- wherein the controller regulates flow of liquid into the fluid line so that the first liquid can be removed from the fluid line and the second liquid can be introduced into the fluid line to suppress biofilm development in the fluid line.

26. A medical or dental apparatus as recited in claim 25, further comprising the first and the second liquid supplies.

27. A medical or dental apparatus as recited in claim 26, wherein the first and the second liquid supplies are disposable containers.

28. A medical or dental apparatus as recited in claim 25, wherein the fluid line is disposable.

* * * * *